United States Patent [19]

Shaked et al.

[11] Patent Number: 4,650,758

[45] Date of Patent: Mar. 17, 1987

[54] STABILIZATION OF ENZYMES USEFUL IN THE PRODUCTION OF GLUCOSONE AND OTHER ENZYMATIC PROCESSES

[75] Inventors: Ze've Shaked, Berkeley; Sidney N. Wolfe, Richmond, both of Calif.

[73] Assignee: Cetus Corporation, Emeryville, Calif.

[21] Appl. No.: 653,736

[22] Filed: Sep. 21, 1984

[51] Int. Cl.$^4$ .................. C12P 19/02; C12N 9/96; C12N 9/08

[52] U.S. Cl. ................................. 435/105; 435/188; 435/192

[58] Field of Search ................ 435/105, 192, 190, 188

[56] References Cited

U.S. PATENT DOCUMENTS 4,423,149 12/1983 Amon, Jr. et al. .................. 435/105

OTHER PUBLICATIONS

Applied Biochemistry and Bioengineering, vol. 1, Immobilized Enzyme Principles 1976 pp. 68–70.
Hartman et al., Biochemistry, vol. 6, No. 8, pp. 2439–2448 (1967).

*Primary Examiner*—Lionel M. Shapiro
*Attorney, Agent, or Firm*—Albert P. Hallunin; Elliott L. Fineman; Leona L. Lauder

[57] ABSTRACT

Catalase and pyranose-2-oxidase are stabilized according to the invention by means of chemical treatment which render the enzymes resistant to thermal inactivation or inactivation of glucosone or both.

Stabilized catalase crosslinked with diimido esters, such as dimethyl suberimidate and dimethyl adipimidate are claimed.

The method for stabilizing catalase against thermal inactivation or glucosone inactivation or both comprising gradually adding a crosslinking agent to a catalase solution and maintaining pH and temperature control is claimed.

Stabilized pyranose-2-oxidase amidinated with an amidinating agent such as ethyl acetimidate is claimed.

A method for stabilizing catalase against thermal inactivation comprising gradually adding an amidinating agent to a pyranose-2-oxidase solution preferably with pH control is claimed.

An improved process for producing glucosone from glucose using stabilized catalase or pyranose-2-oxidase or both according to the invention is also claimed.

17 Claims, 5 Drawing Figures

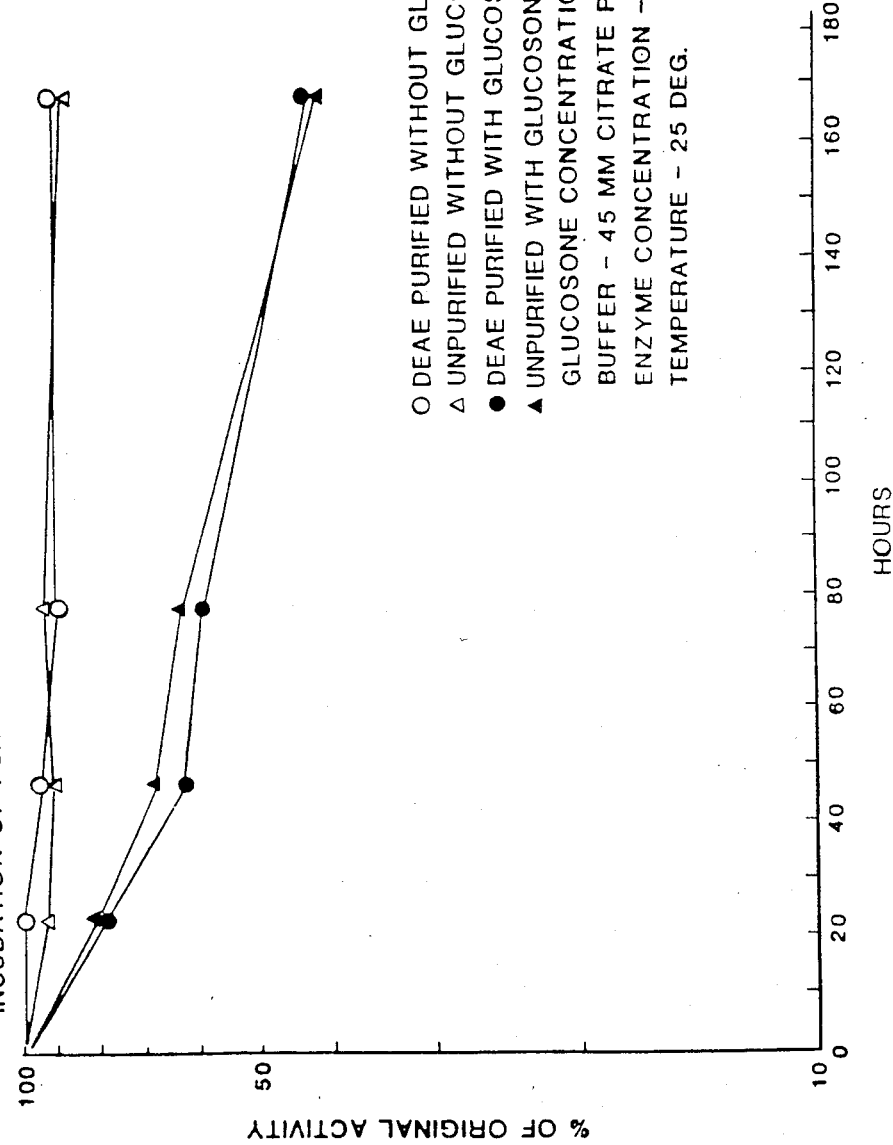

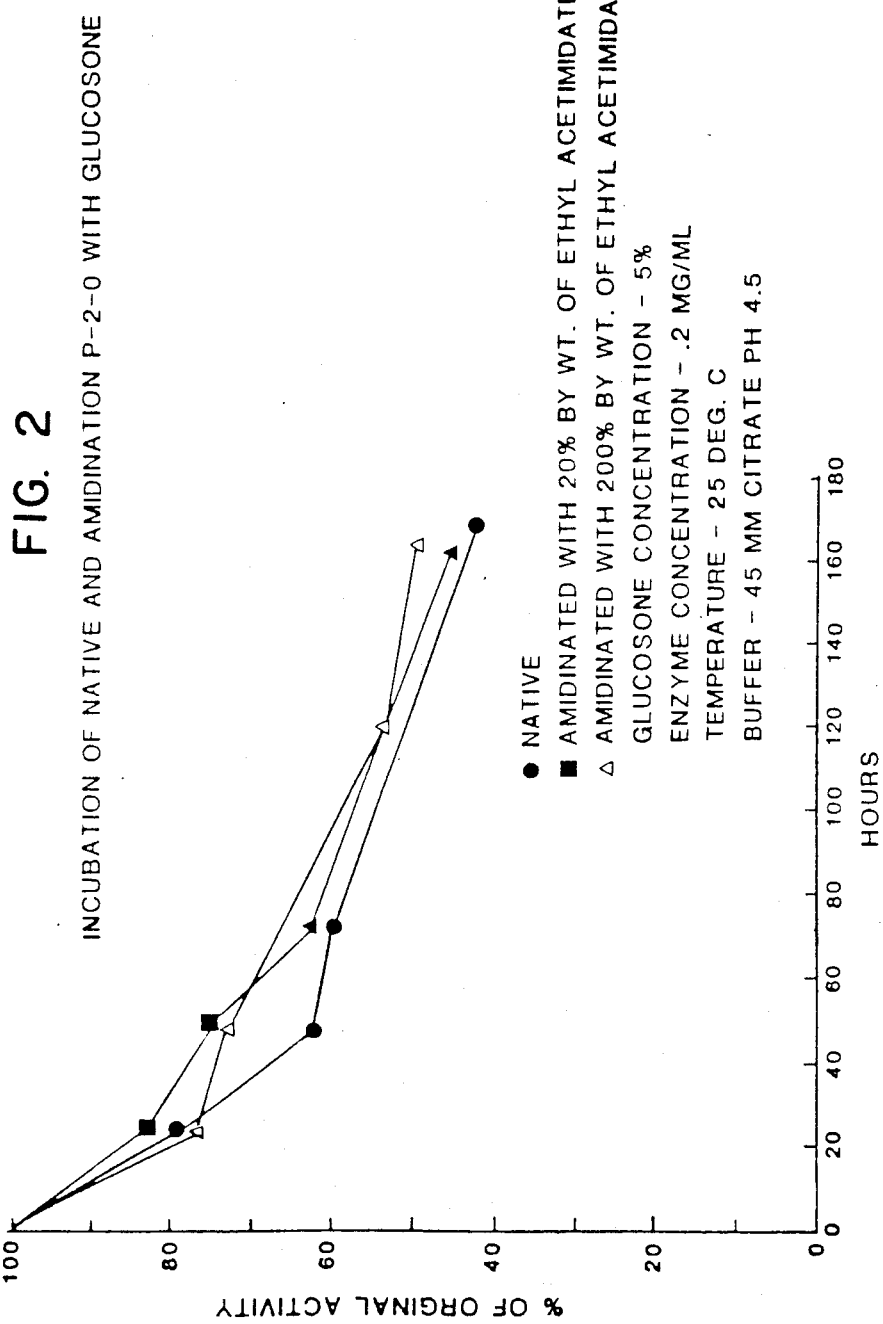

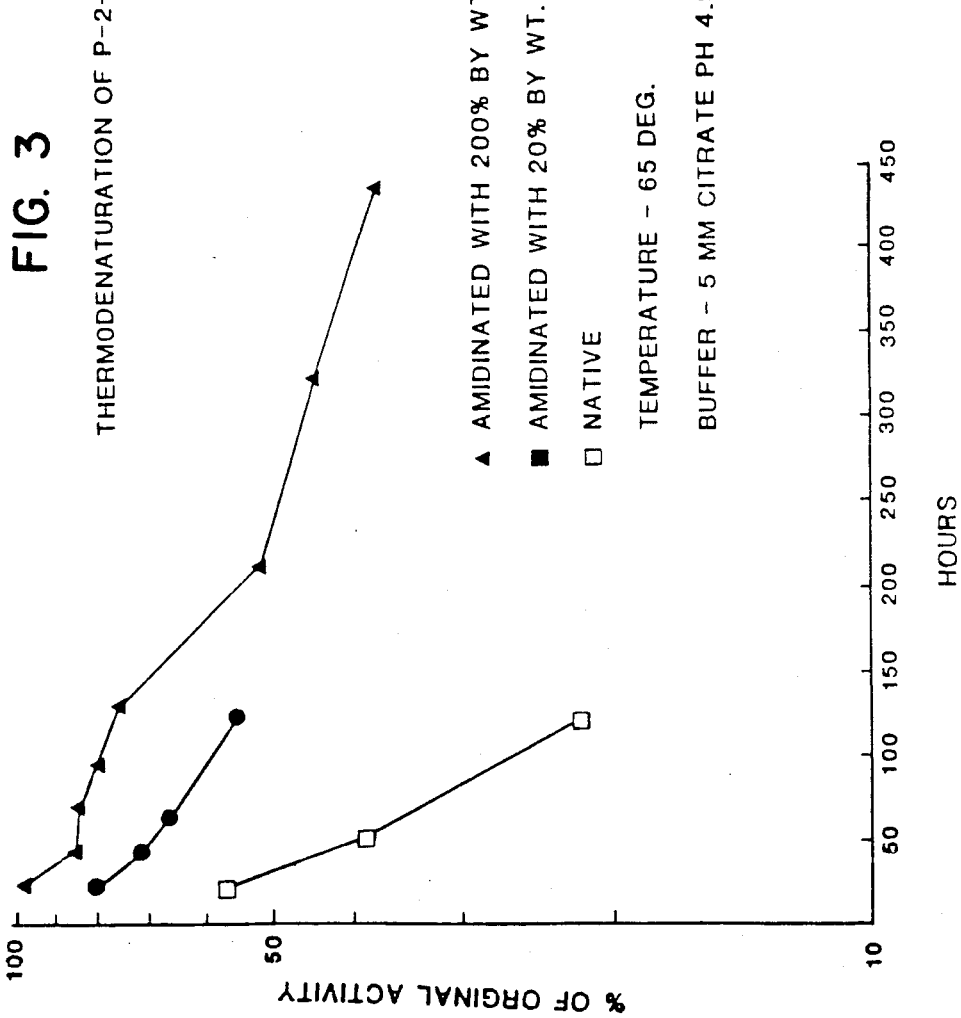

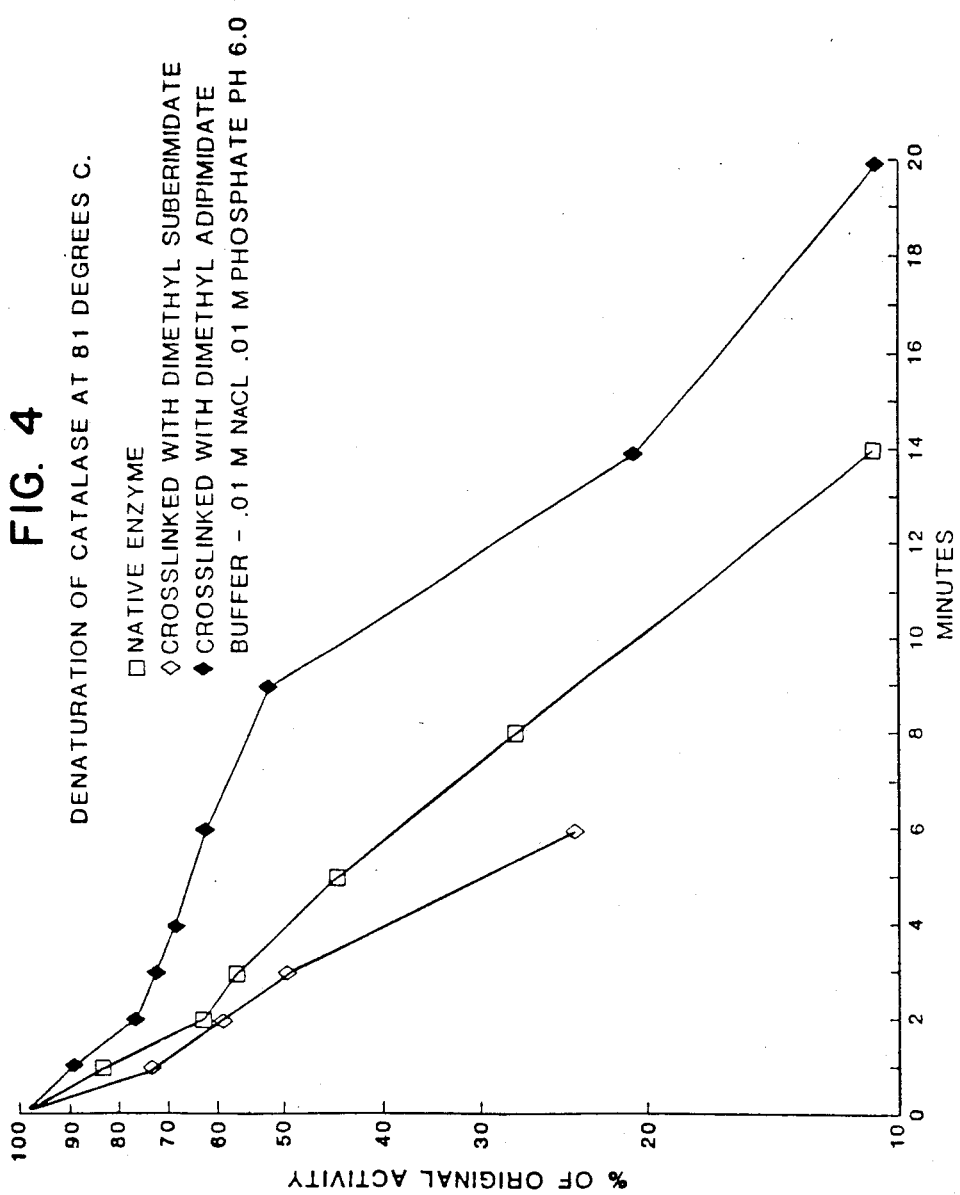

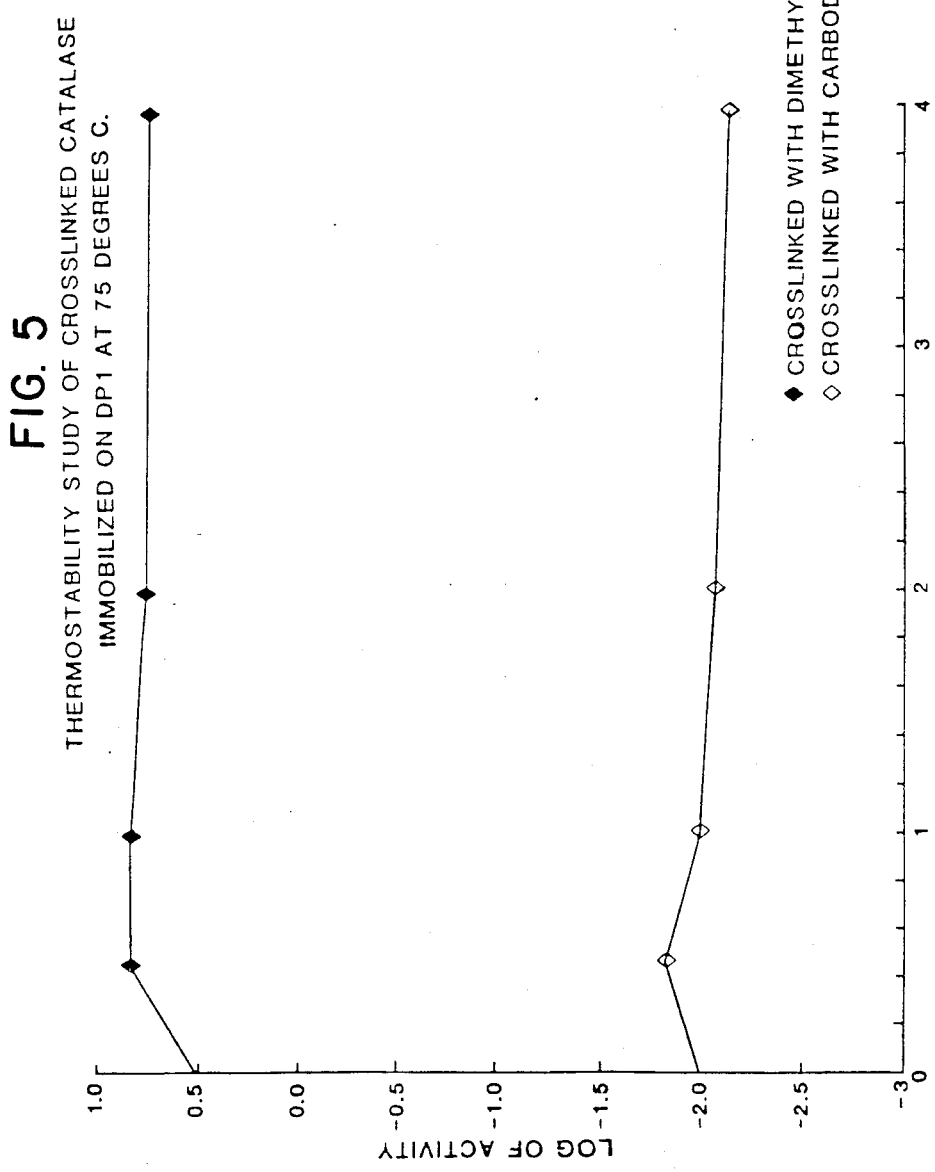

STABILIZATION OF ENZYMES USEFUL IN THE PRODUCTION OF GLUCOSONE AND OTHER ENZYMATIC PROCESSES

FIELD OF THE INVENTION

The invention relates to enzymes stabilized against loss of activity to thermal or end product mediated inactivation. In particular, the invention relates to catalase stabilized by crosslinking with dimethyl diapimidate and pyranose-2-oxidase stabilized by amidination with ethyl acetimidate or its homologues.

BACKGROUND OF THE INVENTION

Catalase-(EC 1.11.1.6) is a tetrameric enzyme with a total molecular weight (MW) of about 323,000 daltons (d). It is capable of reducing hydrogen peroxide to water and molecular oxygen in the stochiometric reaction.

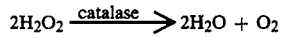

$$2H_2O_2 \xrightarrow{\text{catalase}} 2H_2O + O_2$$

The decomposition of hydrogen peroxide proceeds by a two step reaction catalysed by a heme iron complex that serves as the active site of the enzyme.

Catalase's characteristic activity of decomposing hydrogen peroxide makes it a valuable component in a number of processes. For example, a process for the production of purified oil seed protein according to U.S. Pat. No. 4,464,296 requires treating oil seed protein with sufficient peroxide to increase the solubility of the protein. The solubilized protein is collected, dialysed against water containing catalase, and the dialysate is freeze dried to yield dry purified oil seed protein.

U.S. Pat. No. 4,460,686 describes the oxidation of glucose using an immobilized glucose oxidase-catalase composition in a reaction mixture at temperatures of 1°-2° C. Catalase activity in the process is maintained at least 1/6th of the glucose oxidase activity in the composition. Long reaction life is maintained by running the oxidation at low temperature.

As described in U.S. Pat. No. 4,101,581 catalase is used in a method for determining the presence of substances in fluids, particularly, biological fluids, that form hydrogen peroxide. Catalase and methanol are used to produce formaldehyde from peroxide. The formaldehyde reacts with a hydrozone in the presence of ferric chloride to form a dye that can be determined photometrically.

Catalase and glucose oxidase bound to an appropriate carrier in immediate proximity to one another are used to convert glucose to gluconic acid according to a method described in U.S. Pat. No. 3,935,071. Peroxide produced by the glucose oxide-mediated oxidation of glucose to gluconic acid is convered to water and molecular oxygen by the bound catalase. The coimmobilization of the two enzymes extends the catalyst activity according to the patent and minimizes the inactivation of glucose oxidase by peroxide.

Catalase is also used to convert hydrogen peroxide to water and molecular oxygen in a process for the production of fructose from glucose via the intermediate glucosone, as described in U.S. Pat. Nos. 4,246,347 and 4,423,149. In these patents glucose is reacted with enzymes capable of converting the hydroxyl group at the two position of glucose to a carbonyl in the presence of oxygen. Enzymes capable of carrying out this specific conversion include pyranose-2-oxidase (P-2-0) and glucose-2-oxidases (G-2-0s). Hydrogen peroxide, produced as one product of the enzymatic reaction mediated by P-2-0, oxidizes certain critical sites on the P-2-0 enzyme molecule, damaging its function. Catalase is added to the reaction solution to remove the hydrogen peroxide. The process described in these patents can be conducted within a temperature range from about 15° C. to about 65° C.

Catalase is also used in a process for enhancing the properties of tobacco as described in U.S. Pat. No. 3,889,689. In this process catalase and a liquid containing hydrogen peroxide is forced to permeate the interstices of tobacco where the catalase and hydrogen peroxide react in situ.

A positive image photographic process which uses layers containing catalase is described in U.S. Pat. No. 3,694,207. In this process catalase reacts with hydrogen peroxide to form an image of gas bubbles in the layer, or to produce a dye image by a color-forming oxidation reaction. The catalase is inactivated upon exposure to light.

From the foregoing, it is clear that the enzyme catalase is used in numerous process in which the activity of the enzyme must be maintained without inactivation for at least some period of time during the process. The irreversible dissociation of enzymes into subunits is known to inactivate enzymes. Catalase, a four subunit enzyme is certainly inactivated by dissociation into subunits. The intramolecular crosslinking of enzymes by bifunctional crosslinking reagents is an important tool in the field of enzyme immobilization and stabilization against inactivation.

The effect of crosslinking on the activity and the characteristics of an enzyme, is difficult if not impossible to predict. Crosslinking of one enzyme may yield activity enhancement while crosslinking of a second enzyme may yield no enhancement or even loss of activity. In fact, crosslinking may even cause increased activity and decreased activity in a single bifunctional enzyme. For example, bovine pancreatic ribonuclease A was crosslinked with the bifunctional di-imido ester dimethyl adipimidate. The resulting crosslinked monomeric enzyme displayed an increase in specific activity toward cytidine 2',3'-cyclic phosphate and a decrease in activity toward RNA. Hartman, F. C. and Wold, F. Cross-linking of Bovine Pancreatic Ribonuclease A with Dimethyl Adipimidate, *Biochemistry*, 6(8):2439-2448 (1967).

Thermal inactivation of enzymes may take place at elevated temperatures. By the term elevated temperatures is meant temperatures significantly higher than the temperature that is normally ambient for the organism from which the enzyme was obtained. Thermal inactivation is an important phenomenon in industrial enzymatic processes for a number of reasons.

Chemical and enzymatic reaction rates generally accelerate as temperature increases. If thermal inactivation is prevented, a temperature increase from 25°-70° C. will yield a 100-fold increase in the reaction rate. Thus, from the standpoint of process economics, the use of high temperatures in commercial enzymatic processes is advantageous.

The probability of bacterial contamination is reduced in enzyme reactors run at high temperatures. The deleterious effects of such bacterial contamination are many and include, for example, the liberation of enzyme degrading proteases, the plugging of filters, the production of unwanted by-products and increased cost of the process cycle. Because of the severity of this problem in the food industry, most enzymatic food processes are carried out at temperatures in excess of 60° C.

Process productivity may be increased by maximizing the concentration of dissolved substate in an enzyme reactor. The soluability of most substrates increases with temperature. For example, starch, a polymer of glucose, is gelatinized at temperatures between 100°–110° C.

Examples of industrial processes carrying out elevated temperatures include the production of high-fructose syrup from glucose using glucose isomerase, and alpha amylase and glucoamylase-catalysed hydrolysis of starch.

SUMMARY AND OBJECTS OF THE INVENTION

The inventors have found that catalase crosslinked by certain crosslinking agents has new and unexpected properties as compared with native catalase. Among these new and unexpected properties are stabilization of crosslinked catalase against thermal inactivation, increase in the specific activity of crosslinked catalase compared to other crosslinked catalases, and increased enzyme stability in the presence of inactivating substances, in particular, D-arabino-2-hexosulose (D-glucosone herein referred to as glucosone).

Thermal stabilization as used herein means either a reduction in the rate constant of thermal inactivation of an enzyme under given conditions, an increase in the half-time of thermal inactivation of an enzyme under given conditions, or an increase in the temperature which is necessary to reach a certain extent of thermal inactivation of an enzyme under given conditions. In particular, the inventors have found that catalase crosslinked under certain conditions with dimethyl suberimidate or dimethyl adipimidate, is stable in the presence of glucosone. In addition, such crosslinked catalase shows increased activity in a range of about 115–120% over its activity at time zero over extensive periods of time in the presence of glucosone. In addition to the above mentioned characteristics of crosslinked catalase, the inventors have found that catalase crosslinked with dimethyl adipimidate has increased stabilization against thermal inactivation, and higher specific activity than catalase crosslinked by carbodiimide and dimethyl suberimidate.

The invention further includes a method for crosslinking catalase whereby the crosslinked catalase has the characteristics mentioned above. The method employs as the crosslinking agent, dimethyl adiapimidate or dimethyl suberimidate. If dimethyl suberimidate is employed in the method according to the invention, the crosslinked catalase will have the characteristics of increased stability and activity in the presence of glucosone. If dimethyl adipimidate is employed in the method according to the invention, the resulting crosslinked catalase will have the characteristics of increased stability and activity in the presence of glucosone, increased stabilization against thermal inactivation and higher specific activity than catalase crosslinked by carbodiimide or dimethyl suberimidate.

With respect to the method of crosslinking catalase according to the invention, satisfactory crosslinking of catalase using dimethyl adiapimidate or dimethyl suberimidate requires control for the temperature of the catalase solution during addition of the crosslinker, control of the pH of the catalase solution during addition of the crosslinker, and gradual addition of the crosslinker to the catalase solution.

When catalase was crosslinked with 2% by weight of dimethyl suberimidate added all at once at pH 7, the half-life of catalase in the presence of 4% glucosone at 40° C. in 50 mM acetate improved by only a factor of two (from 50 to about 100 hr). Higher amounts of the crosslinker (5–30% by weight) and performing the reaction at higher pH values (9–10) did not significantly improve the stability of the enzyme in the presence of glucosone. The crosslinking imidine bonds are resistant to hydrolysis. The crosslinker, however, will react with water to form an ester, thus preventing it from crosslinking the protein. In a pH 10 borate buffer (made with about 80% $D_2O$) at room temperature, the half-life of the dimethyl suberimidate is about 2.5 hr as measured by NMR.

In the method according to the invention the temperature of the catalase solution should be maintained in a range between 0° and 10° C. and preferably between 0° and 5° C. pH control should be maintained during addition of the crosslinker in a range between 9.1 and 9.9 to minimize formation of esters between the crosslinker and water, which prevents the crosslinker from reacting with the enzyme. Preferably, pH will be maintained between 9.4 and 9.7. The crosslinker will be added gradually to the catalase solution rather than added all at once. Preferably, an addition of 20% by weight of dimethyl suberimidate or dimethyl adipimidate is added over a period of 5 hours. More gradual additions of crosslinker are of course possible for the same weight percentage of the crosslinker. Shorter addition times are also possible for smaller weight percentages of crosslinker. The optimal time will vary depending on the amount of crosslinker to be added and can be determined experimentally, but in all cases a gradual addition time is preferred, so that only a low concentration of unreacted linker is present when added to the enzyme solution.

Pyranose-2-oxidase (hereinafter P-2-0) is an enzyme that catalyses the oxidation of glucose to glucosone by a two electron mechanism using oxygen as the electron acceptor. Hydrogen peroxide formed as a by-product of this reaction is known to inactivate P-2-0. The use of P-2-0 in an enzymatic conversion of glucose to fructose is described in U.S. Pat. Nos. 4,446,347 and 4,423,149 which are herein incorporated by reference. P-2-0 from *Polyporous obtusus* is a homotetramer with a total MW of 290,000 d. The MW of the subunits is 72,000 and the enzyme contains four flavins. Like catalase, the irreversible dissociation of the enzyme into subunits is known to inactivate the enzyme. However, unlike catalase, the crosslinking of P-2-0 with dimethyl adipimidate or dimethyl suberimidate does not result in stabilization of the enzyme against thermal inactivation or inactivation by the end-product glucosone.

The inventors have found that P-2-0 that has been chemically treated with amidinating agents is stabilized against thermal inactivation as compared to either crosslinked P-2-0 or native P-2-0. In particular P-2-0 that has been treated with ethyl acetimidate retains between 75% and 98% of the activity shown by native P-2-0 when incubated at 25° C. After 100 minutes at 65° C. amidinated P-2-0 retains activity of between 55% and 80% of initial activity whereas native P-2-0 retains only about 22% of initial activity. After 450 minutes at 65° C. amidinated P-2-0 still retains about 50% of its initial activity.

The inventors have further found that amidinated P-2-0 is also stabilized against inactivation by the end-product glucosone as compared to native P-2-0. In the presence of glucosone, the enzymatic activity of P-2-0 decreases in biphasic kenetic mode as shown in FIG. 1. During the first 48 hours, the activity decreases with an apparent half-life of about 70 hours. After 48 hours, the activity has a half-life of about 250 hours. As shown in FIG. 2 after amidination, P-2-0 has a slightly increased apparent half-life.

The invention further includes a method for amidinating P-2-0 whereby the amidinated P-2-0 has the characteristics mentioned above. The method according to the invention employs amidinating agents such as, for example, acetimidate and its homologues including for example ethyl acetimidate. It is believed the methyl acetimidate will also be effective in the practice of the method according to the invention.

The amidination method according to the invention comprises amidinating P-2-0 with an appropriate amidinating agent such as, for example, ethyl acetimidate. The amidinating agent is added gradually while maintaining pH at between 9 and 10.5. Preferably, pH will be maintained at between 9.5 and 10.0.

It is an object of the invention to provide the enzyme catalase stabilized against glucosone and/or thermal inactivation.

It is another object of the invention to provide the enzyme catalase stabilized against glucosone and/or thermal inactivation through the use of a crosslinking agent.

It is an object of the invention to provide the enzyme P-2-0 stabilized against glucosone inactivation and thermal inactivation.

It is another object of the invention to provide the enzyme P-2-0 stabilized against glucosone and thermal inactivation through the use of an amidinating agent.

It is a further object of the invention to provide an improved process for the enzymatic production of glucosone using the enzyme catalase stabilized against glucosone or thermal inactivation.

It is yet a further object of the invention to provide an improved process for enzymatic production of glucosone using the enzyme P-2-0 stabilized against glucosone and thermal inactivation.

BRIEF DESCRIPTION OF THE DRAWINGS

These and other objects of the invention will become more clear from the following examples, which are intended by the inventors to be exemplary only and nonlimiting, and from the following figures in which:

FIG. 1 is a graph of residual activity of native purified and unpurified P-2-0 in the presence of the end-product glucosone;

FIG. 2 is a graph of residual activity of native and amidinated P-2-0 in the presence of the end-product glucosone;

FIG. 3 is a graph of residual activity of native and amidinated P-2-0 at a thermal inactivation temperature;

FIG. 4 is a graph of residual activity of native and crosslinked catalase at a thermal inactivation temperature; and FIG. 5 is a graph of residual activity of catalase crosslinked with dimethyl adipimidate or carbodiimide.

EXAMPLE I

A. Amidination of Pyranose-2-oxidase

P-2-0 was prepared in accordance with the method described in U.S. Pat. No. 4,423,149 and was purified by elution from a DEAE ion exchange column. The column was equilibrated with 25 mM Tris-HCl buffer at pH 8.5 by pumping buffer through the column until the inlet and the outlet pH and conductivity are the same. Prior to loading on the column, the P-2-0 was dialysed against 25 mM Tris-HCl at pH 8.5 so that the pH and ionic strength of the enzyme and starting buffer are the same. The dialysed enzyme was loaded onto the column. The column was eluted with a linear salt gradient consisting of 3 bed volumes of the same buffer having an initial NaCl concentration of zero and a final NaCl concentration of 0.2M. The flow rate was adjusted to 2.5 ml/min. 10 ml fractions of the eluent were collected and analysed for enzyme activity and protein concentration.

Glucosone, (9.8% glucosone, 0.3% glucose, 89% pure as determined by chromatography on an Aminex column was prepared as described in U.S. Pat. No. 4,423,149. Ethyl acetimidate was obtained from Aldrich Chemical Company.

Amidination of P-2-0 with ethyl acetimidate was done by two different methods. In the first method, 23 mg of ethyl acetamidate (0.2 mmol in absolute ethanol) was added slowly with a peristaltic pump over a 5 hour period to 20 ml of P-2-0 at a concentration of 6 mg/ml in 10 mM acetate. The pH of the reaction mixture was maintained at 9.5 by adding 20 mM NaOH using a Chemtrix pH controller. All additions were carried out at 25° C. One hour after the final addition of ethyl acetimidate, the reaction mixture was chromatographed on a G-25 Sephadex column with dilute citrate buffer. The fraction containing the amidinated P-2-0 was retained for assay of activity.

In the second method a solution of ethyl acetimidate (115 mg in 1 ml absolute ethanol) was added in 0.1 ml portions every 30 minutes to 15 ml of P-2-0 at a concentration of 4 mg/ml in 10 mM acetate buffer at pH 5.0. The pH was maintained as above but at pH 10.0. 2.5 hours after the final addition of ethyl acetimidate, the solution was chromatographed as described above. The fraction containing the amidinated P-2-0 was retained for an assay of activity.

B. Determination of Amidination of P-2-0 with Trinitrobenzene Sulfonic Acid (TNBS)

The TNBS determination of amino groups was done by following the procedure described by Habeeb. Habeeb, A. F. S., *Analyt. Biochem.*, 14:382 (1966). TNBS and bovine serum albumin (BSA) were obtained from Sigma Chemical Company, St. Louis, MO. 63178 USA. The amount of P-2-0 used was determined by Lowery assay. To 1 ml of P-2-0 solution at a concentration of 0.6-1 mg/ml were added 1 ml of 4% NaHCO$_3$ at pH 8.5, and 1 ml of 0.1% TNBS. The solution was allowed to react at 40° C. for 2 hours; then 1 ml of 10% sodium dodecyl benzene sulfonate (SDS) was added to solubilize the protein and prevent its precipitation on addition of 0.6 ml of 1N HCl. The absorbance of the solution was read at 335 nm against a blank treated as above but with 1 ml of water (or buffer) instead of the protein solution. A molar extinction coefficient of $1 \times 10^4 M^{-1} cm^{-1}$ was used to calculate the residual amino groups. BSA was used as a standard to verify the results with P-2-0 and to compare the standard with that of Habeeb supra. The results for BSA were within 10% of Habeeb's, however the BSA preparation used by Habeeb was different from the one used herein.

C. Assay of P-2-0

P-2-0 assays were done using a coupled reaction system in which the $H_2O_2$ generated by P-2-0-catalyzed oxidation of glucose was consumed in the oxidation of orthodianisidine (ODAD) to form a colored product, catalyzed by horseradish peroxidase (HRP). Sufficient HRP was used to assure that the second, color-forming reaction was not rate controlling. The reaction was monitored at 460 nm; P-20 activity could be transformed dimensionally from $A_{460}/s$ to $M^{-1} cm^{-1}$, determined from the net absorbance increase observed when known amounts of $H_2O_2$ were added to the assay solution in the absence of P-20. Before running an assay a P-2-0 sample was diluted with phosphate buffer (50 mM pH 6.0) to a concentration of 0.02–0.04 mg/ml of enzyme. Because the half-life of the enzyme in dilute solutions at room temperature is about one to two hours, assays were run immediately after dilution. The 0.1 ml dilute enzyme solution was added to 0.9 ml of a solution that contained 0.01% ODAD, 0.1 mg/ml horseradish peroxidase, and 4.2% glucose in air-saturated 50 mM phosphate buffer at pH 6.0. After 10 minutes at 25° C. the reaction mixtue was quenched by adding 1.0 ml of 2% sulfamic acid. The absorbance at 460 nm was determined against a blank made up with buffer instead of the enzyme solution. The amount of hydrogen peroxide produced was determined by making up standard hydrogen peroxide solutions and mixing them with ODAD-glucose-HRP solution followed by 2% sulfamic acid solution about 1 minute later. Standards were measured at different concentrations and the automatic concentration determination features of the Perkin Elmer Lamda 5 spectrophotometer were used. The standard samples had a standard deviation of less than 2% while samples generally had a standard deviation of less than 5%.

D. Thermodenaturation of Native and Amidinated P-2-0

A 1 ml sample of native P-2-0 or amidinated P-2-0 at a concentration of 5 mg/ml protein in 5 mM citrate at pH 4.9 was transferred to a 1.5 ml Eppendorf test tube and placed in a 65° C. water bath. At various time points the residual activity of the enzyme was centrifuged and then assayed using the ODAD assay described above.

E. Incubation with Glucosone

A 2 ml sample of native P-2-0 or amidinated P-2-0 at a concentration of 0.2 mg/ml in 45 mM citrate buffer at pH 4.5 and 3% glucosone, was placed in a small polypropylene tube and incubated at 25° C. water bath. The control solution contained the same enzyme solution but no glucosone.

F. The Effect of Glucosone on Native P-2-0

In the presence of glucosone the enzymatic activity of P-2-0 decreased in biphasic kinetic mode (FIG. 1). During the first 48 hours the activity decreases with an apparent half-life of about 70 hours. After 48 hours, however, the activity had a half-life of about 250 hours.

Since the decrease in activity might be due to the presence of contaminating pyranose dehydratase two different P-2-0 preparations were used. The first P-2-0 preparation had most of its pyranose dehydratase removed by a DEAE column (0.021 U/min mg) while the second one was an unpurified enzyme preparation (1.4 U/min mg). No significant differences were seen in the inactivation of the enzyme in the presence of glucosone (FIG. 1). The biphasic decrease in activity suggests that there are at least two different inactivation mechanisms caused by glucosone. These results suggest, however, that the inactivation of P-2-0 in the presence of glucosone is a major problem.

G. The Effect of Glucosone on Amidinated P-2-0

The two different amidinated preparations of P-2-0 described above have stabilities in the presence of glucosone that are better than native P-2-0 (FIG. 2). Only $9\pm2$ amino groups per P-2-0 molecule (tetramer) of the extensively amidinated P-2-0 react with TNBS, while with native P-2-0 TNBS reacts with $170\pm1$ amino groups.

H. Thermodenaturation of Native, Amidinated and Crosslinked P-2-0

The amidinated P-2-0 preparations show considerably greater thermostability (FIG. 3) than native P-2-0. Apparently amidination enhances the thermostability of the enzyme. The chemical modification of P-2-0 with higher levels of amidination results in enzyme preparations that are approximately ten times more thermostable than native P-2-0.

EXAMPLE II

Stabilization of Catalase with Diimidate

A. General

Catalase was obtained from Fermco (lot 4927). Dimethyl suberimidate, dimethyl adipimidate, trinitrobenzene sulfonic acid (TNBS), and bovine serum albumin (BSA) were obtained from Sigma. Glucosone was obtained by the method described in U.S. Pat. No. 4,423,149.

B. Assays

Catalase activity was assayed by monitoring the disappearance of the absorbance of hydrogen peroxide at 215 nm. A 50 $\mu l$ aliquot of catalase 5 mg/ml solution was diluted 1 to 3 with 50 mM phosphate buffer at pH 7 to a final concentration of 1.25 mg/ml. 50 $\mu l$ of this diluted enzyme solution was added to 5 ml of 0.003% $H_2O_2$ in phosphate buffer (50 mM pH 7). The blank sample contained 50 $\mu l$ of diluted sample in 5 ml of the same phosphate buffer without $H_2O_2$. The absorbtion at 215 nm was measured every 12 seconds for 3 minutes. The first order rate constant was obtained by averaging ln Ao/At)/t or by using a linear least squares fit. The specific activity U/mg protein was obtained by dividing the rate constant by the milligrams of protein in the peroxide solution. A standard deviation of about 5% was obtained for a given sample. The catalase obtained from Fermco had an activity of about 500 U/mg protein.

C. Crosslinking of Catalase Diimido Esters

A 20 ml sample of catalase at a concentration of 3 mg/ml in 10 mM citrate buffer at pH 5 was run over a G-25 column and then cooled down to 0°–5° C. The crosslinker dimethyl suberimidate or dimethyl adipimidate at a concentration of 18 mg/ml in 2 ml of methanol was added over a period of about 5 hours with a peristaltic pump. The pH was maintained between 9.4–9.7 with a pH controller which automatically added 25 mM NaOH when the pH fell below 9.5. One hour after the last addition of crosslinker, the reaction solution was again run over a G-25 column (with 5–10 mM citrate, pH 5.0) to remove excess crosslinker and salts. All of the protein eluted from the column.

D. Determination of Amino Groups with Trinitrobenzene Sulfonic Acid (TNBS)

The TNBS determination of amino groups was done by following the procedure described above in Example I except that all catalase samples were first chromatographed in a G-25 column to remove any ammonium sulphate and small peptide fragments.

E. Thermodenaturation of Native and Crosslinked Catalase

Catalase or crosslinked catalase at a concentration of 0.2 mg/ml in 0.01M NaCl, 0.01M phosphate buffer at pH 6.0 was placed in 300 μl polyethylene Eppendorf test tubes and put in an 81° C. water bath for a timed interval. Vials, when removed from the bath, were cooled quickly and then assayed after dilution.

F. The Thermostability of the Crosslinked Catalase

Thermostability studies were done at 81° C. with catalase crosslinked with the soluble diimido ester as described above. Crosslinking the enzyme with dimethyl adipimidate results in a appreciably improved thermostable catalase (FIG. 4). Crosslinking the enzyme with dimethyl suberimidate does not result in a catalase which is more stable than the native enzyme.

EXAMPLE III

Thermostability of Adipimidate Crosslinked Catalase Immobilized on DP-1 Methacrylate Supports

A. Immobilization on DP-1 Methacrylate Supports

Catalase, crosslinked as described above with dimethyl adipimidate was adsorbed to Amberlite DP-1 (methacrylic acid-divinylbenzene copolymer, Alfa products lot 0/080) ion exchange resin that had been previously equilibrated in 0.012M Na OAC at a pH between 4.8 and 5.2 by addition of concentrated HCl or NaOH as appropriate. Decanting, resuspension and readjustment of pH of the exchange resin was continued until pH was stable between 4.8 and 5.2 when fresh buffer was added.

Enzyme adsorption was carried out in one of two methods. In the first, a pre-weighed quantity of DP-1 resin was swirled or stirred with a 2–3 times larger volume of catalase in 0.01M NaOC at pH 5 for 5–15 minutes and allowed to settle. After measuring the enzyme concentration in the supernatant by spectrophotometry, another aliquot of enzyme from a more concentrated stock solution was added and mixing resumed. The strategy was to keep adding enzyme until the supernatant absorbance increased proportionally with enzyme added. A graph of supernatant enzyme absorbance versus quantity of enzyme added per mass of exchanger gives a titration curve, initially horizontal because all or most protein is adsorbed, and finally rising linearly with a slope indicative of the protein extinction coefficient. This method depended on rapid equilibration of enzyme with exchanger.

As it was discovered that the DP-1 exchange resin equilibrated slowly—on the time scale of hours to days a second immobilization strategy was used as follows. Swirling of DP-1 was started with a quantity of the crosslinked catalase previously determined to be in excess of exchanger capacity. Supernatant spectra were taken at intervals of hours to days until the rate of absorbance decline became negligible. Adsorption kinetics were followed at 25° C., and the beakers (normally agitated at 100–200 rpm on a shaker table) were carefully sealed with parafilm to minimize evaporation. Supernatant samples were returned after spectral measurement, to maintain a constant volume. Fines, generated through attrition during swirling, were clarified by spinning the sample for 5 minutes in an Eppendorf Model 5412 micro-centrifuge before scanning if there was any sign of suspended matter. After it was clear that the DP-1 adsorbed significant amounts of catalase on the time scale of hours to days, non-kinetic adsorptions were performed without any agitation. Several ml of dimethyl adipimidate-crosslinked catalase solution were simply allowed to stand with a somewhat smaller volume of resin particles. Often adsorption was done with steri-filtered (0.2μ meter pore size) crosslinked catalase and DP-1 previously autoclaved in a foil-covered small glass beaker, using sterile transfers to minimize bacterial contamination. When DP-1 exchanger resin had been loaded with immobilized crosslinked enzyme, it was washed repeatedly in 0.01M NaOAc to remove any bulk unadsorbed enzyme. Specific activity in $M^{-1} s^{-1}$ was calculated from specific activity in $min^{-1}$ g dry weight support $^{-1}$ liter by dividing by 60×/min., dividing by g wet weight/g dry weight, dividing by mg enzyme adsorbed/g wet weight, and multiplying by $3.23 \times 10^8$ mg enzyme/mole enzyme.

B. The Thermostability of the Crosslinked Catalase on an Insoluble Support

Adipimidate-crosslinked catalase was immobilized on DP-1 methacrylate resin beads as described above. The thermostability studies of the immobilized crosslinked catalase were done at 75° C. The immobilized enzyme with crosslinked dimethyl adipimidate results in an appreciably improved thermostable catalase. Crosslinking the enzyme with dimethyl suberimidate using the same procedure as above, does not result in a more thermostable catalase. Moreover, adipimidate crosslinked catalase has substantially greater specific activity than carbodimide crosslinked catalase and is shown in FIG. 5. The introduction of the six carbon chain of adipimidate probably results in a more rigid configuration of the protein than the introduction of an eight carbon chain by suberimidate.

EXAMPLE IV

Coimmobilization of Crosslinked Catalase and Amidinated P-2-0 and Production of Glucosone Crosslinked catalase and amidinated P-2-0 produced as described above in Example I and II may be immobilized on DP-1 resin using the procedure described for catalase immobilization in the previous example. It is preferable that catalase be added in substantial excess to the amount of P-2-0. In general, the catalase/P-2-0 molar ratio can be from 1:1 to 10:1 and the two stabilized enzymes are immobilized simultaneously by adding a quantity of the two stabilized enzymes in the desired molar ratio, which exceeds the determined capacity of the resin for bound protein. The capacity of the resin for bound protein can be determined by supernatant protein spectra as described in Example III. Supernatant protein spectra are taken until the rate of absorbance decline for soluble protein becomes negligable. Addition of the protein to the DP-1 resin is followed at 25° C. The loaded resin is washed as described in Example III. The immobilized stabilized enzymes can be placed in a sterile fermentor and a sterile 10% glucose solution will be added. Sterile filtered oxygen gas or air is bubbled through the glucose solution. The temperature of the fermentor is maintained at a constant temperature between 15° and 65° C. Samples of the reaction mixture will be withdrawn periodically and assayed by HPLC for glucose and glucosone.

An identical assay will be run using nonstabilized P-2-0 and catalase. Higher amounts of glucosone will be produced in the fermentor with the stabilized enzymes as temperature of the fermentations increased.

It will be apparent to those skilled in the art to which this invention pertains that catalase, stabilized as described hereinabove may be used with benefit in numerous applications in which te decompositon of hydrogen peroxide is desirable. For example, the stabilized catalase can be used to extend the effective life of enzymatic fermentations that require catalase. Furthermore, the efficiency of such enzymatic fermentations can be increased by running the fermentation at elevated temperatures that would rapidly inactivate native catalase.

Specifically with respect to the enzymatic production of glucosone using stabilized catalase, it will be apparent that the stabilized enzyme may be used in the process immobilized to a support such as, for example, agarose or other polymeric supports commonly used for enzyme immobilization. Alternatively, stabilized catalase may be used in the process in soluble form without immobilization to a solid support.

It will furthermore be apparent to those skilled in the art to which the invention pertains, that in the enzymatic production of glucosone using stabilized P-2-0, the stabilized P-2-0 may be used in the process immobilized to a support such as, for example, agarose or other polymeric supports commonly used for enzyme immobilization. Alternatively, stabilized P-2-0 may be used in the process in soluble form without immobilization to a solid support.

It will also equally be apparent to those skilled in the art to which the invention pertains that in the enzymatic production of glucosone using the stabilized enzymes described herein, either catalase or P-2-0 may be stabilized. Thus, stabilized catalase may be used in combination with native P-2-0 or stabilized P-2-0 may be used in combination with native catalase. At elevated temperatures, use of either or both of the stabilized enzymes is expected to produce more glucosone than use of both enzymes in their native form.

Other useful variations of the invention in addition to those described herein will be apparent to those skilled in the art to which this invention pertains without departing from the scope of the invention as claimed hereinbelow. Such variations are intended to fall within the scope of the appended claims.

We claim:

1. Stabilized catalase comprising catalase crosslinked by dimethyl suberimidate or dimethyl adipimidate wherein said crosslinked catalase is stabilized against inactivation by glucosone.

2. Stabilized catalase of claim 1 wherein said crosslinked catalase is stabilized against thermal inactivation by dimethyl adipimidate.

3. Stabilized catalase of claim 1 wherein said dimethyl adipimidate crosslinked catalase has a higher specific activity than non-crosslinked catalase.

4. In a process for the conversion of glucose to glucosone using pyranose-2-oxidase and catalase, the improvement comprising providing the stabilized catalase of claim 1.

5. In a process for the conversion of glucose to glucosone using pyranose-2-oxidase and catalase, the improvement comprising providing the stabilized catalase of claim 2.

6. A method of stabilizing catalase against inactivation by glucosone comprising providing a solution of catalase to be stabilized gradually adding dimethyl suberimidate or dimethyl adipimidate to said catalase under conditions that minimize reaction of the diimido ester with water to form esters.

7. The method of claim 6 wherein the diimido ester is dimethyl adipimidate and said crosslinked catalase is stabilized against thermal inactivation.

8. The method of claim 6 wherein said catalase crosslinked wilth either dimethyl suberimidate or dimethyl adipimidate has a higher specific activity than non-crosslinked catalase.

9. The method of claim 6 wherein said conditions that minimize reaction of the diimido ester with water comprise adding said diimido ester at a rate wherein only a low concentration of linker is present in solution.

10. The method of claim 9 wherein the pH is maintained between 9.7 and 9.9 and temperature is maintained between 0° C. and 10° C.

11. Pyranose-2-oxidase stabilized against thermal inactivation by glucosone by aminidating with acetimidate or a homolog thereof.

12. Pyranose-2-oxidase of claim 11 wherein said homolog of acetimidate is selected from the group consisting of methyl and ethyl acetimidate.

13. A method for stabilzing pyranose-2-oxidase against thermal inactivation and inactivation by glucosone comprising providing a solution of pyranose-2-oxidase to be stabilized, and gradually adding acetimidate or a homolog thereof to said solution of pyranose-2-oxidase so that only a low concentration of said acetimidate or homolog thereof is present in solution.

14. The method of claim 13 wherein said homolog of acetimidate is selected from the group consisting of methylacetimidate and ethylacetimidate.

15. In a process for the conversion of glucose to glucosone using pyranose-2-oxidase and catalase, the improvement comprising providing the stabilized pyranose-2-oxidase of claim 11.

16. In the process according to claim 25, the improvement comprising providing the stabilized catalase of claim 1.

17. In the process according to claim 15, the improvement comprising providing the stabilized catalase of claim 2.

* * * * *